United States Patent
Elomari et al.

(10) Patent No.: US 6,720,468 B2
(45) Date of Patent: Apr. 13, 2004

(54) PROCESS FOR THE REMOVAL OF CONJUGATED OLEFINS FROM A MONOOLEFIN STREAM

(75) Inventors: Saleh A. Elomari, Fairfield, CA (US); Richard N. Reynolds, Jr., Point Richmond, CA (US); Steven J. Herron, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 09/892,177

(22) Filed: Jun. 26, 2001

(65) Prior Publication Data

US 2002/0165420 A1 Nov. 7, 2002

Related U.S. Application Data

(60) Provisional application No. 60/215,583, filed on Jun. 30, 2000.

(51) Int. Cl.[7] .................................. C07C 7/152
(52) U.S. Cl. .................. 585/809; 585/864; 585/324; 585/422; 585/421

(58) Field of Search ................. 585/809, 864, 585/324, 422, 421, 424

(56) References Cited

U.S. PATENT DOCUMENTS 5,300,126 A * 4/1994 Brown et al. ............. 44/449

* cited by examiner

Primary Examiner—Walter D. Griffin
Assistant Examiner—Tam Nguyen
(74) Attorney, Agent, or Firm—Conley Rose, PC; Rodney B. Carroll; Joe D. Hulett

(57) ABSTRACT

A process for the separation of conjugated olefins from monoolefins in a fluid comprising such conjugated olefins and monoolefins using a Diels-Alder reaction to provide a fluid comprising a Diels-Alder adduct and monoolefins. The fluid comprising such Diels-Alder adduct and monoolefins can be subjected to a separating means to thereby recover a resulting monoolefin-containing fluid containing less than about 50 parts per million conjugated olefins. The process is particularly useful for purification of fluids containing normal alpha olefins.

20 Claims, 2 Drawing Sheets

Reaction Assembly 1 for Butadiene Removal from 1-Butene

Reaction Assembly 2 for Butadiene Removal from 1-Butene Stream

PROCESS FOR THE REMOVAL OF CONJUGATED OLEFINS FROM A MONOOLEFIN STREAM

This application claims the benefit of U.S. provisional application No. 60/215,583, filed on Jun. 30, 2000.

BACKGROUND OF THE INVENTION

The invention relates to a process for the removal of conjugated olefins from a monoolefin stream such as a stream containing normal alpha olefins.

Monoolefins such as normal alpha olefins can be obtained from streams that have been subjected to, for example, dehydrogenation, cracking, or ethylene oligomerization. Depending upon the production method, the normal alpha olefin stream can contain varying amounts of conjugated olefins. If present in large amounts, the conjugated olefins may be separated from the monoolefins for sale or other use. Methods useful for such a separation include distillation, selective adsorption, selective hydrogenation of the conjugated olefin, dimerization of the conjugated olefin, or complexation of the conjugated olefin.

However, it is very difficult to reduce the conjugated olefins content in a normal alpha olefin stream to low levels by means such as distillation because some isomers have very close boiling points and may form azeotropes with one another preventing complete separation. It is particularly difficult to reduce the levels of conjugated olefins in monoolefin streams below a few hundred parts per million (ppm) by the methods mentioned above. Conjugated olefins can be very undesirable impurities in monoolefins such as normal alpha olefins even in very low concentrations such as a few hundred ppm. Normal alpha olefins (NAOs) are used for applications such as polymerization of monomers to form polyolefins. Examples include polymerization of ethylene to form polyethylene and polymerization of propylene to form polypropylene. Normal alpha olefins such as 1-butene, 1-hexene, and 1-octene, are used in the polyethylene process to provide branching of the resultant polymer. Any conjugated olefin present in a stream containing normal alpha olefins can have a very undesirable impact on the production of polyolefins through catalyst deactivation thus reducing catalyst productivity or by causing crosslinking of the polymer.

As mentioned above, one method currently used to remove conjugated olefins from olefin streams is by selective hydrogenation. Conjugated olefins can be selectively hydrogenated under the proper conditions and using an appropriate catalyst. Selective hydrogenation allows one to greatly reduce the levels of conjugated olefins in the olefin stream. One commercial process that uses selective hydrogenation is UOP's DeFine process. Selective hydrogenation has the disadvantage in that it is difficult to selectively hydrogenate all of the conjugated olefin without hydrogenating significant amounts of monoolefin or isomerizing a normal alpha olefin to an internal olefin. On the other hand, if one minimizes hydrogenation of the monoolefins significant amounts of conjugated olefins are left unconverted.

Dimerization of the conjugated olefin is also a possible way to remove such conjugated olefin from a monoolefin stream. However, this method does not reduce the conjugated olefin content to very low levels.

For the reasons discussed above, it would be very desirable to have an efficient and economical separation/purification process for the removal of even very low levels of conjugated olefins from a monoolefin stream. The present invention provides such a process.

SUMMARY OF THE INVENTION

The present invention relates to a process for the removal of conjugated olefins from a monoolefin-containing fluid. The process of the present invention employs the use of a Diels-Alder dienophile to selectively react with the conjugated olefins to form a Diels-Alder adduct. The Diels-Alder adduct can then be separated or removed from the monoolefin-containing fluid by conventional separation means such as distillation, adsorption, membrane separation and the like and combinations thereof. Another means to accomplish the separation or removal of conjugated olefins from a monoolefin-containing fluid is through the application of the invention using a Diels-Alder dienophile in a reactive distillation.

The present invention comprises a process for removing conjugated olefins from a fluid containing such conjugated olefins and monoolefins to provide a monoolefin-containing product depleted in conjugated olefins, comprising:

(a) contacting a fluid comprising conjugated olefins and monoolefins with a Diels-Alder dienophile to provide a fluid comprising a Diels-Alder adduct and monoolefins;

(b) separating the monoolefins from the fluid comprising a Diels-Alder adduct and monoolefins of (a); and (c) recovering a resulting monoolefin-containing fluid depleted in conjugated olefins.

Alternatively, the process of the present invention can be characterized as a process for the separation of conjugated olefins and monoolefins, comprising:

contacting a fluid comprising monoolefins and conjugated olefins with a Diels-Alder dienophile to provide a fluid comprising a Diels-Alder adduct and monoolefins; and recovering a resulting monoolefin-containing fluid comprising less than about 50 ppm of conjugated olefins.

The present invention provides a method to efficiently reduce the levels of conjugated olefin-contaminant or contaminants in a resulting monoolefin-containing fluid to very low levels without substantial losses of the monoolefin and without introducing other contaminants. Surprisingly the present invention is able to effectively reduce the conjugated diene levels of the resulting monoolefin-containing product to less than about 50 ppm. The process of the present invention utilizes a minimum of new equipment and can utilize existing separation methods to provide the required separation of the adduct from the mixture comprising such adduct and monoolefins.

DETAILED DESCRIPTION OF THE INVENTION

Figure 1:
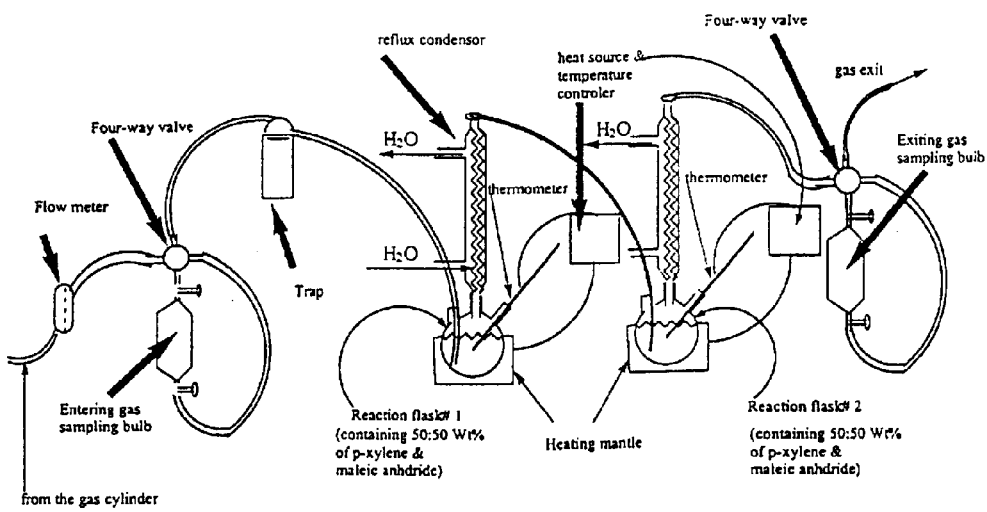
FIG. 1 is a schematic of the apparatus used for Examples 1 and 2.

The process of the present invention comprises the use of a Diels-Alder type reaction to remove conjugated olefins from a monoolefin-containing fluid. The monoolefin-containing fluid may comprise a single monoolefin or may comprise a mixture of more than one monoolefin structure. The term "fluid" denotes gas, liquid, vapor, or combinations thereof. The Diels-Alder type reaction utilizes a dienophile, preferably a Diels-alder dienophile, to react with a conju gated diene (conjugated olefin) to form a Diels-Alder adduct. An example of the reaction is as follows:

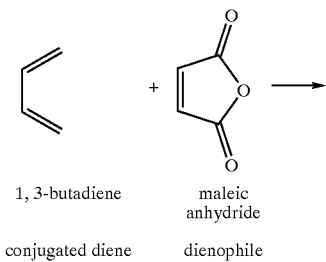

1, 3-butadiene    maleic anhydride conjugated diene    dienophile

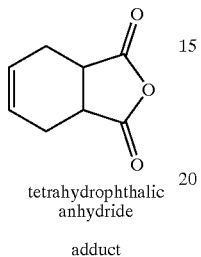

tetrahydrophthalic anhydride adduct

The term "Diels-Alder dienophile" refers to any dienophile which can be used in the Diels-Alder reaction described herein. The term "Diels-Alder adduct" refers to any adduct which is provided according to the Diels-Alder reaction described herein.

Examples of suitable dieneophiles include, but are not limited to ethylenes, acetylenes, cyclics, and the like and combinations thereof. Examples of suitable ethylenes include, but are not limited to, ethylenes having a general structure $R^1R^2C=CR^3R^4$ where $R^1$=H, C(=O)OR$^5$, C(=O)R$^6$, C(=O)NR$^7$R$^8$, CN, $C_1$ to $C_{30}$ alkyl, and aromatic, $R^2$=H, C(=O)OR$^5$, C(=O)R$^6$, C(=O)NR$^7$R$^8$, CN, $C_1$ to $C_{30}$ alkyl, and aromatic, $R^3$=H, C(=O)OR$^5$, C(=O)R$^6$, C(=O)NR$^7$R$^8$, CN, $C_1$ to $C_{30}$ alkyl, and aromatic, $R^4$=H, C(=O)OR$^5$, C(=O)R$^6$, C(=O)NR$^7$R$^8$, CN, $C_1$ to $C_{30}$ alkyl, and aromatic, $R^5$=$C_1$ to $C_{10}$ alkyl, aromatic, and (H)C=CH$_2$, $R_6$=$C_1$ to $C_{10}$ alkyl, aromatic, and (H)C=CH$_2$, $R^7$=$C_1$ to $C_{10}$ alkyl, aromatic, and $R^8$=$C_1$ to $C_{10}$ alkyl, and aromatic.

Examples of suitable ethylenes include, but are not limited to, methyl acrylate, ethyl acrylate, methyl methacrylate, ethyl methacrylate, vinyl acrylate, dimethyl fumarate, dimethyl maleate, diethyl fumarate, diethyl maleate, diphenyl fumarate, divinyl fumarate, divinylmaleate, acrolein, methyl vinyl ketone, divinylketone, acrylamide, N,N-dimethyl acrylamide, N,N-dimethyl methacrylamide, N,N-diethyl acrylamide, N,N-diethyl acrylamide, acrylonitrile, methacrylonitrile, 1,1-dicyanoethylene, maleonitrile, fumaronitrile, tetracyanoethylene, and the like and combinations thereof.

Examples of suitable acetylenes include, but are not limited to, acetylenes having a general structure $R^1C\equiv CR^2$ where $R^1$=H, C(=O)OR$^3$, C(=O)R$^4$, C(=O)NR$^5$R$^6$, CN, $C_1$ to $C_{10}$ alkyl, and aromatic, $R^2$=H, C(=O)OR$^3$, C(=O)R$^4$, C(=O)NR$^5$R$^6$, CN, $C_1$ to $C_{10}$ alkyl, and aromatic, $R^3$=$C_1$ to $C_{10}$ alkyl, and aromatic, $R^4$=H, $C_1$ to $C_{10}$ alkyl, and aromatic, $R^5$=$C_1$ to $C_{10}$ alkyl, and aromatic, and $R^6$=$C_1$ to $C_{10}$ alkyl, and aromatic.

Examples of suitable acetylenes include, but are not limited to acetylene (ethyne), propyne, 1-butyne, 2-butyne, dimethyl acetylenedicarboxylate, diethyl acetylenedicaboxylate, phenyl acetylene, diphenyl acetylene, and the like and combinations thereof.

Examples of suitable cyclics include, but are not limited to, maleic derivations having a general structure

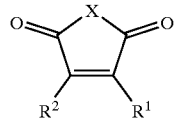

where X=O, N, and S, $R^1$=H, C1 to C10 alkyl, and aromatic, and $R^2$=H, $C_1$ to $C_{10}$ alkyl, and aromatic.

Additional examples of suitable cyclics include, but are not limited to, benzoquinone derivatives having a general structure

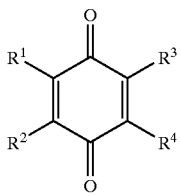

where $R^1$=H, $C_1$ to $C_{10}$ alkyl, aromatic, and (H)C=CH$_2$, $R^2$=H, $C_1$ to $C_{10}$ alkyl, aromatic, and (H)C=CH$_2$, $R^3$=H, $C_1$ to $C_{10}$ alkyl, aromatic, and (H)C=CH$_2$, and $R^4$=H, $C_1$ to $C_{10}$ alkyl, aromatic, and (H)C=CH$_2$.

Examples of suitable maleic derivatives include, but are not limited to, maleic anhydride, methyl maleic anhydride, dimethyl maleic anhydride, maleimide, N-methyl maleimide, N-ethyl maleimide, methyl maleimide, dimethyl maleimide, methyl-N-methyl maleimide, dimethyl-N-methyl maleimide, and the like and combinations thereof.

Examples of suitable benzoquinone derivatives include 1,4-benzoquinone, 2-methylbenzoquinone, 2,3-dimethylbenzoquinone, 2,5-dimethylbenzoquinone, 2,6-dimethylbenzoquinone, 2,3,5-trimethylbenzoquinone, 2,3,5,6-tetramethylbenzoquinone, and the like and combinations thereof.

Preferred dieneophiles useful in a process of the present invention include, but are not limited to, maleic anhydride, derivatives of maleic anhydride, benzoquinone, derivatives of benzoquinone, dialkyl fumarates, dialkyl maleates, dialkylacetylenedicarboxylates, and the like and combinations thereof. More preferred dienophiles useful in a process of the present invention include maleic anhydride, dimethyl acetylene dicarboxylate, benzoquinone, and combinations thereof. The most preferred dienophile useful in a process of the present invention is maleic anhydride.

The term "conjugated olefin" used throughout this specification refers any olefin having at least one pair of double bonds in conjugation. The conjugated olefin may have additional double bonds that may or may not be conjugated. The simplest example of a conjugated olefin is 1,3-butadiene. Examples of suitable conjugated olefins include, but are not limited, conjugated olefins generally comprising at least about four carbon atoms per molecule and no more than about ten carbon atoms per molecule, preferably comprising at least about four carbon atoms per molecule and no more than about eight carbon atoms per molecule, and more preferably comprising at least about four carbon atoms per molecule and no more than about six carbon atoms per molecule.

Examples of suitable conjugated olefins containing four carbon atoms per molecule include 1–3 butadiene. Examples of suitable conjugated olefins containing five carbon atoms per molecule include 1,3-pentadiene and 2-methyl-1,3-butadiene, preferably 1,3-pentadiene.

Examples of suitable conjugated olefins containing six carbon atoms per molecule include, but are not limited to, 1,3-hexadiene, 2,4-hexadiene, 1,3,5-hexatriene, 2-methyl-1,3-pentadiene, 2,3-dimethyl-1,3-butadiene, and 3-methyl-1,3-pentadiene. Preferred conjugated olefins containing six carbon atoms per molecule include 1,3-hexadiene, 2,4-hexadiene, 1,3,5-hexatriene, and the like and combinations thereof. More preferred conjugated olefins containing six carbon atoms per molecule include 1,3-hexadiene.

Examples of suitable conjugated olefins containing seven carbon atoms per molecule include, but are not limited to, 1,3-heptadiene, 2,4-heptadiene, 1,3,5-heptatriene, and the like and combinations thereof. Preferred conjugated olefins containing seven carbon atoms per molecule include 1,3-heptadiene.

Examples of suitable conjugated olefins containing eight carbon atoms per molecule include, but are not limited to, 1,3-octadiene, 2,4-octadiene, 3,5-octadiene, 1,3,5-octatriene, 2,4,6-octatriene, 1,3,5,7-octatetriene, and the like and combinations thereof. Preferred conjugated olefins containing eight carbon atoms per molecule include 1,3-octadiene.

Examples of suitable conjugated olefins containing nine carbon atoms per molecule include, but are not limited to, 1,3-nonadiene, 2,4-nonadiene, 3,5-nonadiene, 1,3,5-nonatriene, 2,4,6-nonatriene, 1,3,5,7-nonatetraene, and the like and combinations thereof. Preferred conjugated olefins containing nine carbon atoms per molecule include 1,3-nonadiene.

Examples of suitable conjugated olefins containing ten carbon atoms per molecule include but are not limited to, 1,3-decadiene, 2,4-decadiene, 3,5-decadiene, 4,6-decadiene, 1,3,5-decatriene, 2,4,6-decatriene, 3,5,7-decatriene, 1,3,5,7-decatetraene, 2,4,6,8-decatetraene, 1,3,5,7,9-decapentaene, and the like and combinations thereof. Preferred conjugated olefins containing ten carbon atoms per molecule include 1,3-decadiene.

The adduct, preferably Diels-Alder adduct, can be separated from the monoolefin-containing fluid by any separating means known in the art capable of separating an adduct from a monoolefin-containing fluid. Examples of suitable separating means include, but are not limited to, distillation, adsorption, membrane separation, and the like and combinations thereof. The adduct typically has a substantially higher molecular weight than the resulting monoolefin-containing fluid being purified. Thus, conventional distillation is generally capable of separating the adduct. Another way to accomplish the separation is by performing the conjugated diene/Diels-Alder dienophile reaction and Diels-Alder adduct separation or removal in a reactive distillation apparatus. For example, the boiling point of 1-butene is −6.3° C. and the boiling point of tetrahydrophthalic anhydride is greater than 100° C. For reference, the boiling point of butadiene is −4.5° C.

The process of the present invention provides a resulting monoolefin-containing fluid or product generally containing less than about 50 parts per million (ppm) of conjugated olefin, preferably less than about 25 ppm of conjugated olefin, more preferably less than about 10 ppm of conjugated olefin, and most preferably less than about 1 ppm of conjugated olefin.

Examples of suitable monoolefins for use in a process of the present invention include, but are not limited to, normal alpha olefins. Examples of suitable normal alpha olefins include, but are not limited to, 1-butene, 1-pentene, 1-hexene, 1-heptene, 1-octene, 1-nonene, 1-decene, and the like and combinations thereof. Preferred normal alpha olefins include 1-butene, 1-pentene, 1-hexene, and combinations thereof.

The conjugated olefins and monoolefins in a fluid comprising such conjugated olefins and monoolefins to be used in a process of the present invention preferably contain the same number of carbon atoms. For example, a preferred fluid for use in a process of the present invention comprises a monoolefin of 1-butene and a conjugated diolefin of 1,3-butadiene.

EXAMPLES

The following tests were performed in order to determine the effectiveness of a process of the present invention in removing conjugated olefins from a fluid comprising such conjugated olefins and monoolefins.

Examples 1 and 2—Apparatus

A 1-butene stream, containing 1,3-butadiene, was passed through two reaction vessels (three-necked round-bottomed flasks) containing a Diels-Alder dienophile solution. The reaction vessels were equipped with a reflux condenser, heating mantel, a thermometer, and a magnetic stirring apparatus. Both reaction vessels were assembled with the 1-butene inlet in the first neck, the reflux condenser mounted on the middle neck, and the thermometer affixed to the third neck. Butene flow control was achieved with a gas flow controller. Temperature control was achieved by connecting the thermometer and heating mantel to a temperature controlled electrical outlet. Feed and treated 1-butene samples were obtained through use of sampling bulbs which could be isolated from the reaction apparatus via use of 4-way valves. The 1-butene flow reaction apparatus elements, for Examples 1 and 2, were connected by Teflon® tubes. A schematic of the apparatus is represented in FIG. 1.

Example 1—Procedure

Two Diels-Alder dieneophile solutions of 75 grams of maleic anhydride, in 75 grams of p-xylene, were heated to 90° C. A 1-butene stream, containing 50 ppm of 1,3-butadiene, was passed through the reaction vessels containing the Diels-Alder dienophile solutions at a flow rate of 0.15 to 0.2 cubic ft/hour. The 1-butene stream and reactor effluent samples were obtained from the feed and exit gas sampling bulbs and analyzed by gas chromatography. The results are summarized in Table 1.

Example 2—Procedure

Example 2 was performed using the same procedure as Example 1 with the following exceptions: a recrystallized maleic anhydride sample was used and the starting 1,3-butadiene concentration was 72 ppm. The results are summarized in Table 1.

Examples 3 through 32—Apparatus

Figure 2:
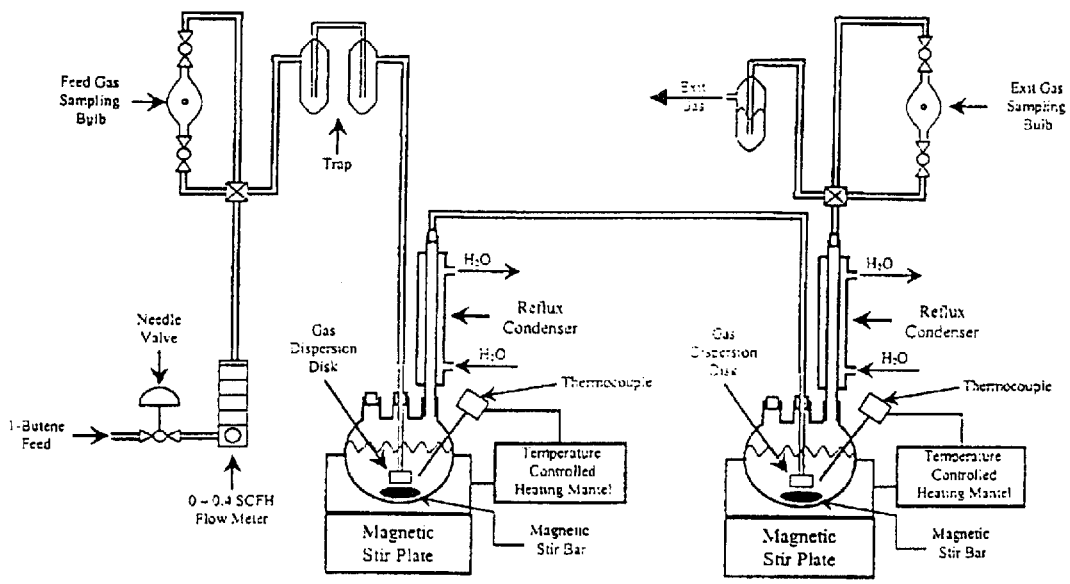
FIG. 2 is a schematic of the apparatus used for Examples 3 through 32.

A 1-butene stream, containing 1,3-butadiene, was passed, through gas dispersion tubes, through two reaction vessels (three-necked round-bottomed flasks) containing a Diels-Alder dienophile. The reaction vessels were equipped with a reflux condenser, heating mantel, a thermocouple, and a magnetic stirring apparatus. Both reaction vessels were assembled with the 1-butene inlet gas dispersion tube located in the center neck, the reflux condenser mounted on the third neck, and the thermometer affixed to the thermometer neck. The first neck was closed with a rubber septum. Butene flow control was achieved with a needle valve and a gas flow controller. Temperature control was achieved by connecting the thermocouple and heating mantel to a temperature controlled electrical outlet. Feed and treated 1-butene samples were obtained through use of sampling bulbs which could be isolated from the reaction apparatus via use of 4-way valves. The 1-butene flow reaction apparatus elements, for Examples 3 through 32, were connected by Teflon® tubes. A schematic of the apparatus is represented in FIG. 2.

Examples 3 through 32—Procedure

A 1-butene stream, containing approximately 67 to 72 ppm of 1,3-butadiene, was passed through the reaction vessels containing the Diels-Alder dieneophile solutions, composed of a Diels-Alder dienophile in a solvent in amounts as recited in Table 1, at a flow rate of 0.2 or 0.4 cubic ft/hour at a temperature of between 60° C. and 148° C. The 1-butene stream and reactor effluent samples were obtained from the feed and exit gas sampling bulbs and analyzed by gas chromatography. The results are summarized in Table 1.

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

What is claimed is:

1. A process for purifying a monoolefin stream, comprising:
    contacting a gaseous monoolefin stream comprising one or more monoolefins with a Diels-Alder dienophile to convert one or more conjugated olefins present in the monoolefin stream to a Diels-Alder adduct;
    and removing the Diels-Alder adduct from the monoolefin stream, thereby purifying the monoolefin stream such that it comprises less than about 50 parts per million (ppm) conjugated olefins.

2. A process according to claim 1 wherein said Diels-Alder dieneophile is selected from the group consisting of maleic anhydride, benzoquinone, dialkyl fumarates, dialkyl maleates, dialkylacetylenedicarboxylates, and combinations thereof.

3. A process according to claim 2 wherein said Diels-Alder dieneophile is maleic anhydride.

TABLE 1

Experimental examples for the removal of conjugated olefins from a monoolefin-containing fluid using a Diels-Alder dieneophile

| Example | Dienophile (amount) | Solvent (amount) | Temp. (° C.) | Flow Rate (cubic ft/hour) | Butadiene level of Exit Fluid (ppm) |
|---|---|---|---|---|---|
| 1 | Maleic Anhydride (75 g) | p-xylene (75 g) | 90 | 0.15–0.20 | 7.0 |
| 2 | Re-crystallized Maleic Anhydride (75 g) | p-xylene (75 g) | 90 | 0.15–0.20 | <1.0 |
| 3 | Maleic Anhydride (75 g) | o-xylene (90 mL) | 90 | 0.2 | 5.7 |
| 4 | Maleic Anhydride (75 g) | o-xylene (90 mL) | 90 | 0.4 | 8.8 |
| 5 | Maleic Anhydride (75 g) | o-xylene (90 mL) | 60 | 0.2 | 6.8 |
| 6 | Diethyl Fumarate (120 g) | o-xylene (120 mL) | 60 | 0.2 | 47.8 |
| 7 | Diethyl Fumarate (120 g) | o-xylene (120 mL) | 90 | 0.2 | 49.3 |
| 8 | Diethyl Fumarate (120 g) | o-xylene (120 mL) | 120 | 0.2 | 31.4 |
| 9 | Dimethyl Acetylene Dicarboxylate (100 mL) | o-xylene (100 mL) | 60 | 0.2 | 46.2 |
| 10 | Dimethyl Acetylene Dicarboxylate (100 mL) | o-xylene (100 mL) | 90 | 0.2 | 30.9 |
| 11 | Dimethyl Acetylene Dicarboxylate (100 mL) | o-xylene (100 mL) | 120 | 0.2 | 16.0 |
| 12 | Maleic Anhydride (75 g) | o-xylene (90 mL) | 90 | 0.2 | 6.4 |
| 13 | Maleic Anhydride (75 g) | o-xylene (90 mL) | 120 | 0.2 | 10.0 |
| 14 | Maleic Anhydride (75 g) | o-xylene (90 mL) | 120 | 0.4 | 14.5 |
| 15 | 1,4-Benzoquinone (100 g) | o-xylene (120 mL) | 90 | 0.2 | 11.7 |
| 16 | 1,4-Benzoquinone (100 g) | o-xylene (120 mL) | 90 | 0.4 | 19.9 |
| 17 | 1,4-Benzoquinone (100 g) | o-xylene (120 mL) | 120 | 0.2 | 12.4 |
| 18 | Phenylacetylene (100 mL) | o-xylene (100 mL) | 60 | 0.2 | 66.1 |
| 19 | Methyl Vinyl Ketone (100 mL) | o-xylene (100 mL) | 60 | 0.2 | 57.3 |
| 20 | Hexadecene (200 mL) | — | 90 | 0.2 | 68.0 |
| 21 | Hexadecene (200 mL) | — | 120 | 0.2 | 70.0 |
| 22 | Hexadecene (200 mL) | — | 148 | 0.2 | 69.8 |
| 23 | Methyl Vinyl Ketone (100 mL) | Hexadecane (100 mL) | 80 | 0.2 | 63.4 |
| 24 | Maleic Anhydride (100 g) | Hexadecane (100 mL) | 60 | 0.2 | 7.1 |
| 25 | Maleic Anhydride (100 g) | Hexadecane (100 mL) | 90 | 0.2 | 6.3 |
| 26 | Maleic Anhydride (100 g) | Hexadecane (100 mL) | 90 | 0.4 | 12.3 |
| 27 | Maleic Anhydride (100 g) | Hexadecane (100 mL) | 120 | 0.4 | 10.7 |
| 28 | Dimethyl Acetylene Dicarboxylate (100 mL) | Hexadecane (100 mL) | 60 | 0.2 | 44.1 |
| 29 | Dimethyl Acetylene Dicarboxylate (100 mL) | Hexadecane (100 mL) | 90 | 0.2 | 29.3 |
| 30 | Dimethyl Acetylene Dicarboxylate (100 mL) | Hexadecane (100 mL) | 90 | 0.4 | 31.9 |
| 31 | Ethyl Propiolate (100 mL) | Hexadecane (100 mL) | 60 | 0.2 | 58.8 |
| 32 | Ethyl Propiolate (100 mL) | Hexadecane (100 mL) | 90 | 0.2 | 64.0 |

4. A process according to claim 1 wherein said conjugated olefins comprise at least about 4 carbon atoms per molecule and no more than about 10 carbon atoms per molecule.

5. A process according to claim 4 wherein said conjugated olefins comprise at least about 4 carbon atoms per molecule and no more than about 8 carbon atoms per molecule.

6. A process according to claim 1 wherein said conjugated olefins are selected from the group consisting of 1,3-butadiene, 1,3-pentadiene, 1,3-hexadiene, 2,4-hexadiene, 1,3,5-hexatriene, 1,3-heptadiene, 2,4-heptadiene, 1,3,5-heptatriene, 1,3-octadiene, 2,4-octadiene, 3,5-octadiene, 1,3,5-octatriene, 2,4,6-octatriene, 1,3,5,7-octatetraene, 1,3-nonadiene, 2,4-nonadiene, 3,5-nonadiene, 1,3,5-nonatriene, 2,4,6-nonatriene, 1,3,5,7-nonatetraene, 1,3-decadiene, 2,4-decadiene, 3,5-decadiene, 4,6-decadiene, 1,3,5-decatriene, 2,4,6-decatriene, 3,5,7-decatriene, 1,3,5,7-decatetraene, 2,4,6,8-decatetraene, 1,3,5,7,9-decapentaene, and combinations thereof.

7. A process according to claim 6 wherein said conjugated olefins are selected from the group consisting of 1,3-butadiene, 1,3-pentadiene, 1,3-hexadiene, 1,3-heptadiene, 1,3-octadiene, 1,3-nonadiene and 1,3-decadiene.

8. A process according to claim 1 wherein said monoolefins comprise normal alpha olefins.

9. A process according to claim 1 wherein said monoolefins are selected from the group consisting of 1-butene, 1-pentene, 1-hexene, 1-heptene, 1-octene, 1-nonene, 1-decene, and combinations thereof.

10. A process according to claim 9 wherein said monoolefins are selected from the group consisting of 1-butene, 1-pentene, 1-hexene, and combinations thereof.

11. A process according to claim 1 wherein said purified monoolefin stream comprises less than about 25 parts per million conjugated olefins.

12. A process according to claim 1 wherein said purified monoolefin stream comprises less than about 10 parts per million conjugated olefins.

13. A process according to claim 1 wherein said is selected from the group consisting of distillation, adsorption, membrane separation, and combinations thereof.

14. A process according to claim 1 wherein said removing is conducted using reactive distillation.

15. A process according to claim 1 wherein said monoolefins are 1-butene and said conjugated olefins are 1,3-butadiene.

16. A process according to claim 15 wherein said dienophile is maleic anhydride.

17. The process according to claim 1 wherein said Diels-Alder dienophile is generally represented by the formula:
$R^1R^2C=CR^3R^4$ where $R^1$=H, $C(=O)OR^5$,$C(=O)R^6$,$C(=O)NR^7R^8$, CN,$C_1$ to $C_{30}$ alkyl, and aromatic, $R^2$=H, $C(=O)OR^5$,$C(=O)R^6$,$C(=O)NR^7R^8$, CN,$C_1$ to $C_{30}$ alkyl, and aromatic, $R^3$=H, $C(=O)OR^5$,$C(=O)R^6$,$C(=O)NR^7R^8$, CN,$C_1$ to $C_{30}$ alkyl, and aromatic, $R^4$=H, $C(=O)OR^5$,$C(=O)R^6$,$C(=O)NR^7R^8$, CN,$C_1$ to $C_{30}$ alkyl, and aromatic, $R^5$=$C_1$ to $C_{10}$ alkyl, aromatic, and $(H)C=CH_2$, $R^6$=$C_1$ to $C_{10}$ alkyl, aromatic, and $(H)C=CH_2$, $R^7$=$C_1$ to $C_{10}$ alkyl, aromatic, and $R^8$=$C_1$ to $C_{10}$ alkyl, and aromatic.

18. The process according to claim 1 wherein said Diels-Alder dienophile is generally represented by the formula:
$R^1C\equiv CR^2$ where $R^1$=H, $C(=O)OR^3$,$C(=O)R^4$,$C(=O)NR^5R^6$, CN, $C_1$, to $C_{10}$ alkyl, and aromatic, $R^2$=H, $C(=O)OR^3$,$C(=O)R^4$,$C(=O)NR^5R^6$, CN, $C_1$, to $C_{10}$ alkyl, and aromatic, $R^3$=$C_1$ to $C_{10}$ alkyl, and aromatic, $R^4$=H, $C_1$ to $C_{10}$ alkyl, and aromatic, $R^5$=$C_1$ to $C_{10}$ alkyl, and aromatic, and $R^6$=$C_1$ to $C_{10}$ alkyl, and aromatic.

19. The process according to claim 1 wherein said Diels-Alder dienophile is generally represented by the formula:

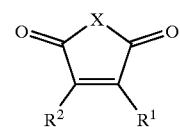

where X=O, N, and S, $R^1$=H, $C_1$ to $C_{10}$ alkyl, and aromatic, and $R^2$=H, $C_1$ to $C_{10}$ alkyl, and aromatic.

20. The process according to claim 1 wherein said Diels-Alder dienophile is generally represented by the formula:

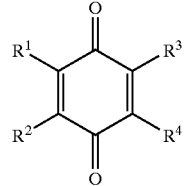

where $R^1$=H, $C_1$ to $C_{10}$ alkyl, and aromatic, and $(H)C=CH_2$, and $R^2$=H, $C_1$ to $C_{10}$ alkyl, aromatic, and $(H)C=CH_2$, $R^3$=H, $C_1$ to $C_{10}$ alkyl, and aromatic, and $(H)C=CH_2$, and $R^4$=H, $C_1$ to $C_{10}$ alkyl, and aromatic, and $(H)C=CH_2$.

* * * * *

UNITED STATES PATENT AND TRADEMARK OFFICE
CERTIFICATE OF CORRECTION

PATENT NO. : 6,720,468 B2
DATED : April 13, 2004
INVENTOR(S) : Elomari et al.

It is certified that error appears in the above-identified patent and that said Letters Patent is hereby corrected as shown below:

<u>Column 9,</u>
Line 36, insert -- removing -- between "said" and "is"

Signed and Sealed this

Fifth Day of April, 2005

JON W. DUDAS
*Director of the United States Patent and Trademark Office*